(12) United States Patent
Melilli et al.

(10) Patent No.: US 11,317,899 B2
(45) Date of Patent: May 3, 2022

(54) BALL-TO-SHAFT QUICK CONNECT ADAPTER FOR SURGICAL RETRACTION TOOLS

(71) Applicant: TERUMO CARDIOVASCULAR SYSTEMS CORPORATION, Ann Arbor, MI (US)

(72) Inventors: Bryan Melilli, North East, MD (US); Timothy J. Canatella, Rising Sun, MD (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 420 days.

(21) Appl. No.: 16/600,810

(22) Filed: Oct. 14, 2019

(65) Prior Publication Data

US 2021/0106318 A1 Apr. 15, 2021

(51) Int. Cl.
- A61B 17/00 (2006.01)
- A61B 90/50 (2016.01)
- A61B 17/02 (2006.01)

(52) U.S. Cl.
CPC .............. *A61B 17/00* (2013.01); *A61B 17/02* (2013.01); *A61B 90/50* (2016.02); *A61B 2017/00477* (2013.01)

(58) Field of Classification Search
CPC ....................... A61B 2018/00172; A61B 17/02
See application file for complete search history.

(56) References Cited

U.S. PATENT DOCUMENTS

| 4,457,300 A | 7/1984 | Budde | |
|---|---|---|---|
| 4,692,073 A * | 9/1987 | Martindell | B25B 21/00 |
| | | | 279/82 |
| 5,011,344 A * | 4/1991 | Johnson | B23B 31/107 |
| | | | 279/82 |
| 6,656,113 B2 | 12/2003 | Green, II et al. | |
| 6,722,667 B2 * | 4/2004 | Cantlon | B25B 15/001 |
| | | | 279/22 |
| 7,018,328 B2 | 3/2006 | Mager et al. | |

(Continued)

FOREIGN PATENT DOCUMENTS

WO 2004052178 A2 6/2004

OTHER PUBLICATIONS

Assistant™ Attachments with StableSoft™ Technology, Terumo Product Brochure, Jan. 2018.
Beating Heart and Surgical Stabilization Product Portfolio, Terumo Product Brochure, Jul. 2015.

*Primary Examiner* — Zade Coley
(74) *Attorney, Agent, or Firm* — Darryl Newell; MacMillan, Sobanski & Todd, LLC

(57) ABSTRACT

A mounting adapter has a proximal end for interfacing with a surgical stabilizer arm and a distal end for interfacing with a tissue manipulator tool. The adapter includes a receiver body defining a bore having an opening at the distal end for receiving the shaft of a manipulator tool. The receiver body has a detent projecting radially into the bore. A ball stem projects at the proximal end and is configured for insertion into a collet of the stabilizer arm. The detent is radially displaceable between 1) a radially outward position when the adapter is in an unlocked state in which the shaft of the manipulator tool is slidable into or out of the bore and 2) a radially inward position when the adapter is in a locked state in which the detent captures the shaft of the manipulator tool.

14 Claims, 13 Drawing Sheets

(56) References Cited

U.S. PATENT DOCUMENTS

| | | | |
|---|---|---|---|
| 7,226,448 B2 | 6/2007 | Bertolero et al. | |
| 7,296,804 B2 * | 11/2007 | Lechot | A61B 17/1666 279/81 |
| 7,585,277 B2 | 9/2009 | Taylor et al. | |
| 7,682,305 B2 | 3/2010 | Bertolero et al. | |
| 7,726,664 B2 * | 6/2010 | Peters | B23B 31/005 279/23.1 |
| 7,749,157 B2 | 7/2010 | Bertolero | |
| 9,498,198 B2 | 11/2016 | Hu et al. | |
| 9,510,895 B2 * | 12/2016 | Houser | A61B 90/08 |
| 2021/0106318 A1 * | 4/2021 | Melilli | A61B 17/00 |

* cited by examiner

BALL-TO-SHAFT QUICK CONNECT ADAPTER FOR SURGICAL RETRACTION TOOLS

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to tissue retractors and stabilizers used for surgical procedures, and, more specifically, to the attachment of retractor/stabilizer tools to the end of a stabilizer arm.

Many different types of surgical procedures are facilitated by mechanical devices to retract, restrain, or otherwise situate tissues and other body structures in and around a surgical site. During cardiac surgery, for example, a sternal retractor is typically mounted over the patient having spaced retractor blades on a frame wherein the blades are inserted into an incision and spread apart for separating the tissues overlying the surgical site. The frame of the sternal retractor has also been used to support additional "rakes" (i.e., retractors) and other fixed tools or devices in order to manipulate organs or tissues within the larger surgical field, as shown in U.S. Pat. No. 5,772,583, for example.

For obtaining compact and strong placement of such tools while avoiding complicated position adjustment mechanisms, a stabilizer arm has been employed having a bendable shaft that is anchored to a fixed frame and having a quick-connect mechanism at its distal end for receiving various attachments (i.e., tools, rakes, suction stabilizers, positioners, and other instruments). The attachments are collectively referred to herein as tissue manipulator tools.

One example of a commercially-available stabilizer arm is the Hercules™ Stabilizing Arm, sold by Terumo Cardiovascular Systems Corporation of Ann Arbor, Mich. This stabilizer arm includes a lockable, articulating column wherein a central tensioning cable is strung through a series of links. When the cable is tensioned (e.g., by rotating a handle), the links move toward each other to interlock via a series of ball and socket joints. The column becomes rigid when the central cable is tensioned. Releasing the tension (e.g., by counter-rotating the handle) returns the column to the flexible state. In the relaxed state, enough tension may be maintained to weakly remain in position as the column is adjusted to a desired configuration. The ball and socket joints are generally hemispherical so that side-to-side adjustment angles are available over a wide range. The stabilizer arm may be reusable for many procedures after being properly sterilized. The quick-connect mechanism at the distal end of the articulating column receives compatible tools that may be either disposable or reusable.

Various types of mechanisms have been adopted for the quick-connect function, including ball-type and shaft-type. For the ball-type, the tool includes a mounting shaft ending in a ball shape that is retained in a collet on the distal end of the stabilizer arm. In an unclamped state, arms of the collet are movable to allow the ball shape to be snapped into the collet. In a clamped state, the collet arms are compressed against the ball to rigidly hold the tool. For the shaft type, the tool ends with a straight shaft which is inserted into an axial bore on the distal end of the stabilizer arm. The shaft is held in the bore by a movable latch or pin in the stabilizer arm that selectably presses against the shaft. The shaft may have an indent or catch on one side to engage the latch.

A typical surgical facility or room may have stabilizer arms available which all employ just one of the types of quick-connect mechanisms. Since tools must be compatible with the quick-connect mechanism, any particular tool can be used only with a particular type of stabilizer arm. Thus, when only one particular type of stabilizer arm is available to a user, only the tools compatible with that particular type can be used. It would be desirable to enable certain tools made for one type of quick connect to be used (i.e., mounted to) a stabilizer arm having a different type of quick connect.

SUMMARY OF THE INVENTION

In one aspect of the invention, a mounting adapter has a proximal end for interfacing with a surgical stabilizer arm and a distal end for interfacing with a tissue manipulator tool. A receiver body defines a bore having an opening at the distal end for receiving the manipulator tool, wherein the receiver body includes a detent projecting radially into the bore. A ball stem projects at the proximal end and is configured for insertion into a collet of the stabilizer arm. The detent is radially displaceable between 1) a radially outward position when the adapter is in an unlocked state in which the shaft of the manipulator tool is slidable into or out of the bore and 2) a radially inward position when the adapter is in a locked state in which the detent captures the shaft of the manipulator tool.

DETAILED DESCRIPTION OF PREFERRED EMBODIMENTS

Figure 1:
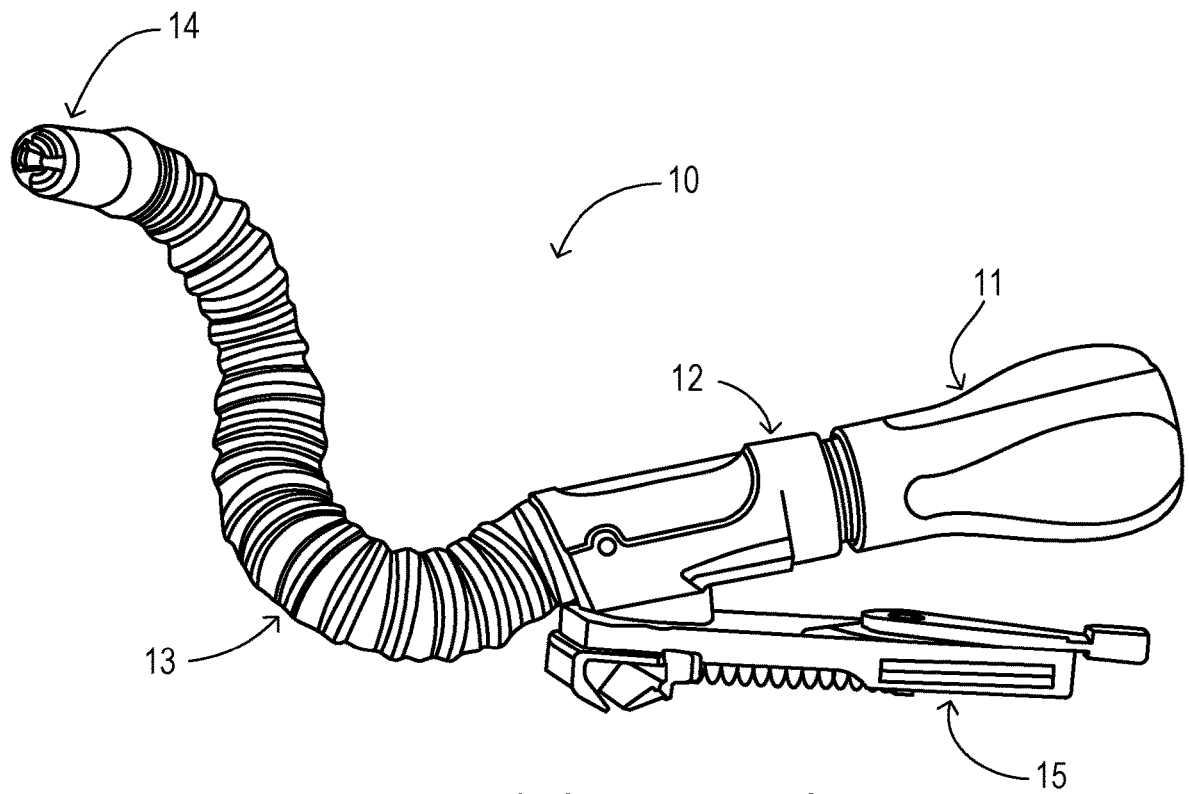
FIG. 1 is a side view of a prior art stabilizer arm with a ball-type quick connect.
Figure 2:
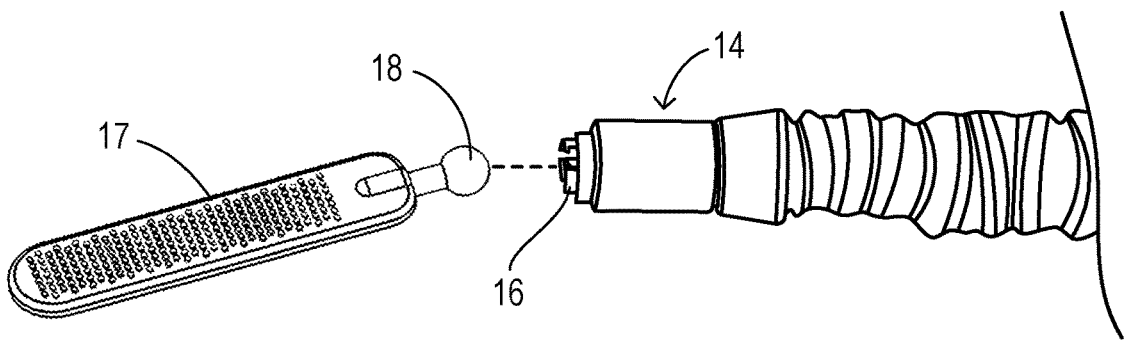
FIG. 2 is a side view of a retractor tool with a ball stem being mounted to the quick connect of FIG. 1.

FIGS. 1 and 2 show a known stabilizing arm 10 with a handle 11, base 12, articulating section 13, and quick-connect mount 14. A clamp assembly 15 attaches to a fixture of a sternal retractor, for example. A tension cable extends from a proximal end of the stabilizing arm (e.g., from the base or handle) to the distal end (e.g., the quick-connect mount or a final fixed link in the adjustable linkage). A solid, stranded cable or a fiber resin can be used. In the example of FIG. 1, an internal mechanism adjusts tension in the cable in response to rotation of handle 11. Articulating section 13 has a plurality of nested, semi-spherical links which can be rotated within one another to provide bends in the direction in which section 13 extends. When the cable is sufficiently slack, the links are slidable but when the cable is tightened then the links bind together and section 13 retains a desired trajectory.

As shown in FIG. 2, quick connect 14 is a ball-type mount with a collet 16 for receiving a ball stem 18 of a manipulator tool 17 (e.g., a malleable finger for grasping tissues). When the tension cable is slack, circumferentially-spaced fingers of collet 16 flex apart to accept insertion or removal of ball stem 18. After tightening of the tension cable, collet 16 retains tool 17 in a fixed configuration.

Figure 3:
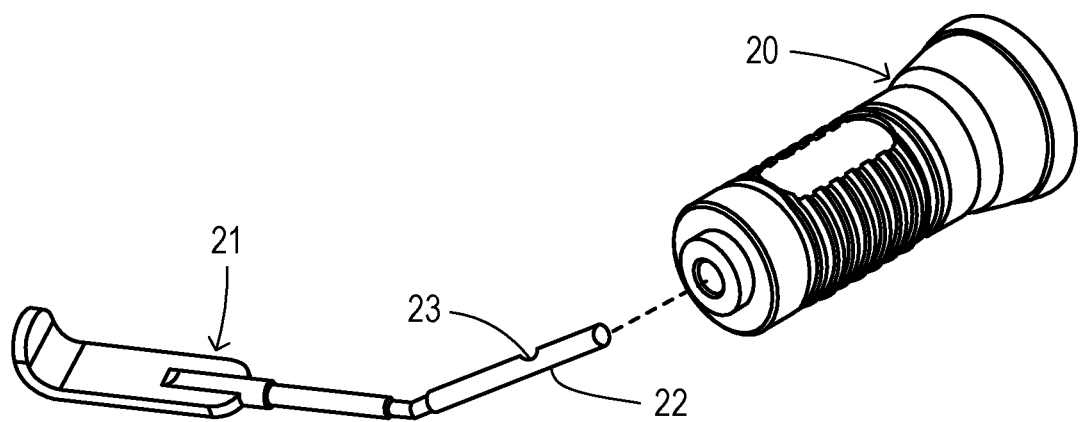
FIG. 3 is a side view of a retractor tool with an end shaft being mounted to a prior art shaft-type quick connect.
Figure 4:
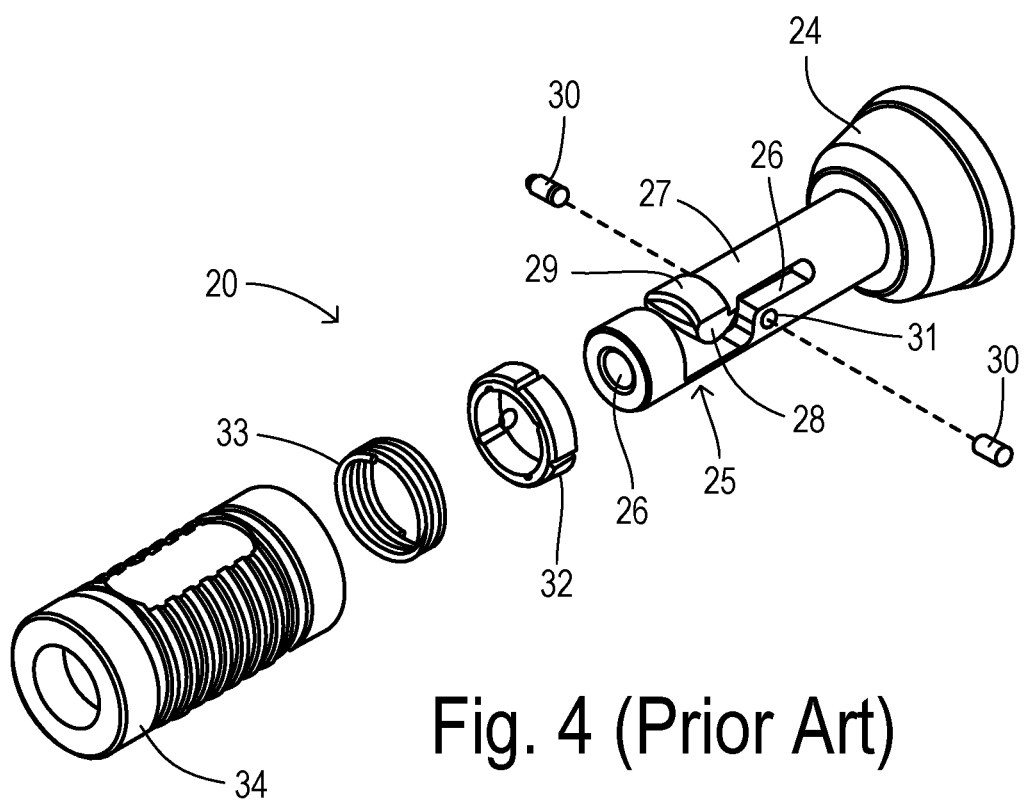
FIG. 4 is an exploded view of the shaft-type quick connect of FIG. 3.
Figure 5:
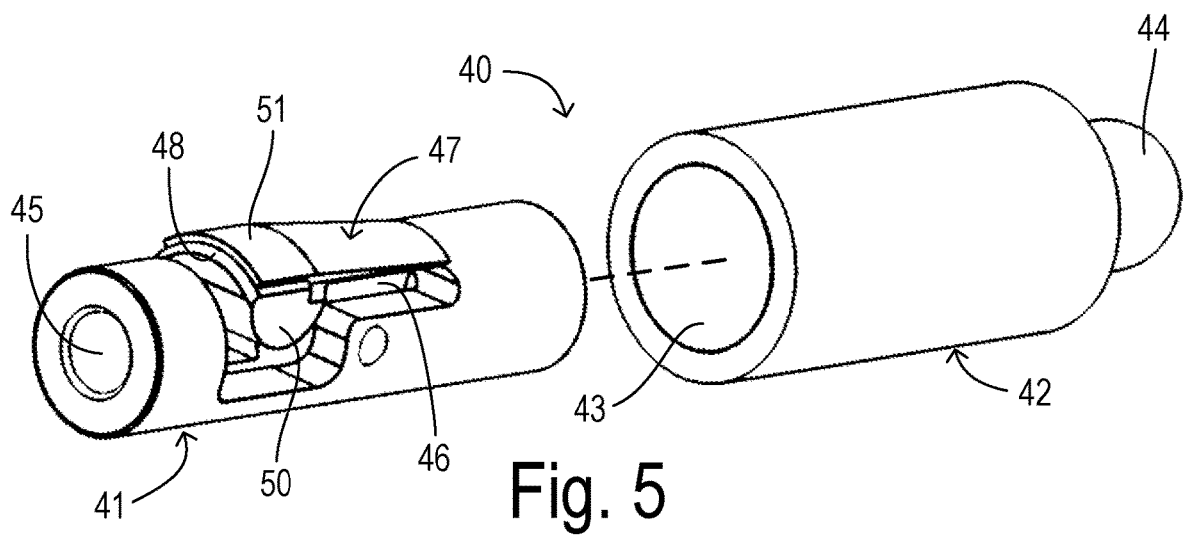
FIG. 5 is a perspective view of a first embodiment of a mounting adapter of the invention, prior to insertion of a receiver body into a cylindrical sleeve.

FIGS. 3 and 4 show another commercially-available mounting system for manipulator tools on a stabilizer arm. As shown in FIG. 3, a shaft-type quick-connect mount 20 receives a manipulator tool 21 (e.g., malleable retractor finger) having a mounting shaft 22 at its distal end. Shaft 22 may preferably include a notch 23 along part of its circumference to be captured by a latch or pin within a socket of quick-connect 20.

FIG. 4 provides an exploded view of mount 20, wherein a base 24 (which is itself attached to an end link of the articulating section of the stabilizer arm) supports a casing 25 defining a hollow passage 26 acting as a socket to receive shaft 22. Passage 26 extends to an outer radial surface at medial portion of casing 25 to form a flexible spring arm or beam 27. At the end of spring arm 27, a detent 28 projects radially inward and a cam surface 29 projects radially outward. In its undeflected (relaxed) state, spring arm 27 is in a position wherein detent 28 does not intrude into passage 26 (i.e., longitudinal insertion/removal of a tool shaft within passage 26 is unobstructed). An inward radial force on cam surface 29 deflects detent 28 into passage 26 for retaining shaft 22 of tool 21. Preferably, notch 23 receives detent 28 for positive locking of shaft 22, but locking can alternatively be achieved by compression of detent 28 against a cylindrical shaft without a notch.

For selectably compressing cam surface 29, a tubular collar 34 is provided. Two pegs 30 are installed in holes 31 to project radially from casing 25 and are received in axial guide slots in an inner hollow surface of collar 34 to guide the axial sliding of collar 34 over casing 25. An inner diameter of tubular collar 34 is tapered so that it is larger at a proximal end and gradually reduces toward the proximal end of collar 34 (opposite base 24). A spring 33 is attached between collar 34 and casing 25 (or base 24) such that spring 33 pulls collar 34 over casing 25 against or toward base 24. An aluminum ring 32 may be affixed at base 24 to hold the assembly together. Interference between cam surface 29 and the tapered portion of collar 34 presses down on spring arm 27 causing detent 28 to project into passage 26. This prevents an attached tool from being inserted or removed until collar 34 is manually pulled away from base 24. Once collar 34 is pulled up, the internal taper collar 34 no longer applies pressure to spring arm 27, and tool shaft 22 can be inserted or removed very easily. When the user stops pulling on collar 34, spring 33 pulls it back down over cam surface 29, thereby locking detent 28 in place.

In order to operate with quick-connect mount 20, a manipulator tool is made with an end shaft (with or without a notch). Since a ball cannot be included at the end of the shaft, such a tool is incompatible with a ball-type quick-connect mount with a collet as shown in FIGS. 1 and 2. The invention provides an adapter that can be fitted to the end shaft of a manipulator tool in order to enable it to be mounted to the collet of the ball-type quick-connect mount.

The present invention provides a mounting adapter having a proximal end with a ball for connecting to a ball-type quick-connect socket of a stabilizer arm and a distal end with a hollow bore for receiving and locking a shaft-type manipulator tool. In particular, the adapter has a receiver body defining a bore having an opening at the distal end for receiving the manipulator tool, wherein the receiver body includes a detent projecting radially into the bore. The bore may be defined within a single tubular receiver body or may be defined by pivoting receiver members (e.g., having a scissor-shape). A ball stem associated with the receiver body projects at the proximal end which is configured for insertion into a collet of the stabilizer arm. The ball stem may be integrally formed with the receiver body or a separate component. In each case, the detent is radially displaceable between 1) a radially outward position when the adapter is in an unlocked state in which the shaft of the manipulator tool is slidable into or out of the bore and 2) a radially inward position when the adapter is in a locked state in which the detent captures the shaft of the manipulator tool.

FIGS. 5-13 show a first embodiment of a mounting adapter 40 comprised of a receiver body 41 and a cylindrical sleeve 42. Sleeve 42 forms a tube with an inner surface defining a socket 43 having an inner diameter that allows sleeve 42 to slide over receiver body 41. Receiver body 41 has a hollow cylindrical wherein a bore 45 extends from an opening at the distal end. A notch 46 (at an intermediate axial location of body 41 spaced away from the distal end) extends from the bore to an outer surface of body 41, thereby creating a cantilever spring 47 (i.e., a living hinge or suspended beam) with a free end 48. A detent 50 is formed on free end 48 extending radially inward. An outer diameter of spring 47 gradually increases toward free end 48 up to a maximum diameter at a lip 51, which is greater than a corresponding inner diameter of sleeve 42 when spring 47 is in a natural, uncompressed state (e.g., spring 47 is shaped as a wedge). Under radial compression, free end 48 of spring 47 can deflect radially inward so that detent 50 moves from an outer radial position (e.g., outside the outer diameter of bore 45) which provides the unlocked state into a position that radially enters bore 45 to bear against a tool shaft which provides the locked state.

Figure 6:
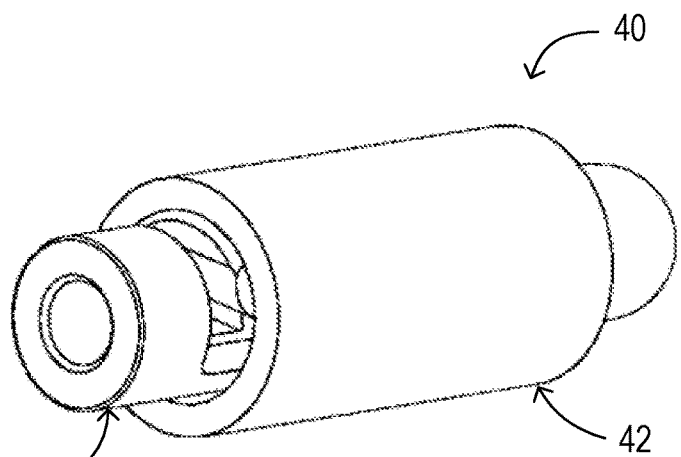
FIG. 6 is a perspective view of the components of FIG. 5 in an assembled state.
Figure 7:
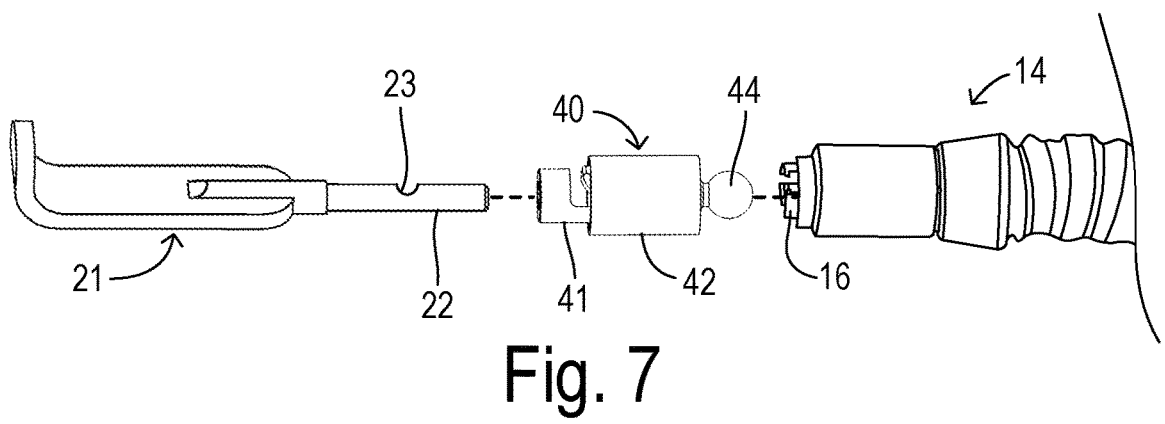
FIG. 7 is a side view showing assembly of the mounting adapter of FIG. 5 with a shaft-type retractor tool and a ball-type quick connect on a stabilizer arm.
Figure 8:
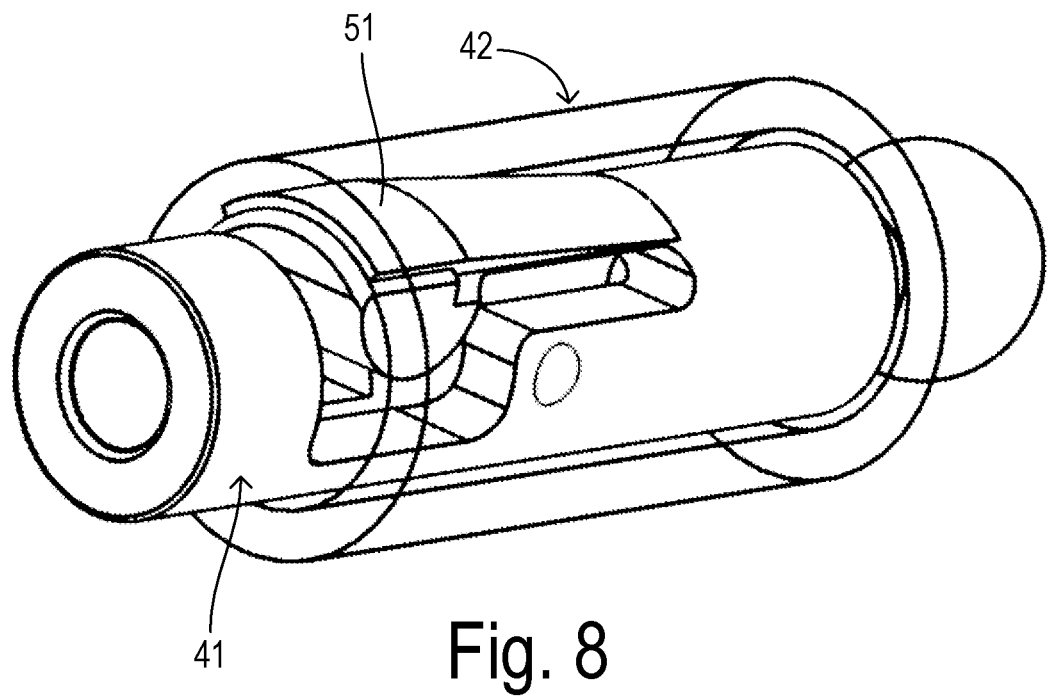
FIG. 8 is a perspective view of the mounting adapter of FIG. 5 with the cylindrical sleeve rendered transparent.
Figure 9:
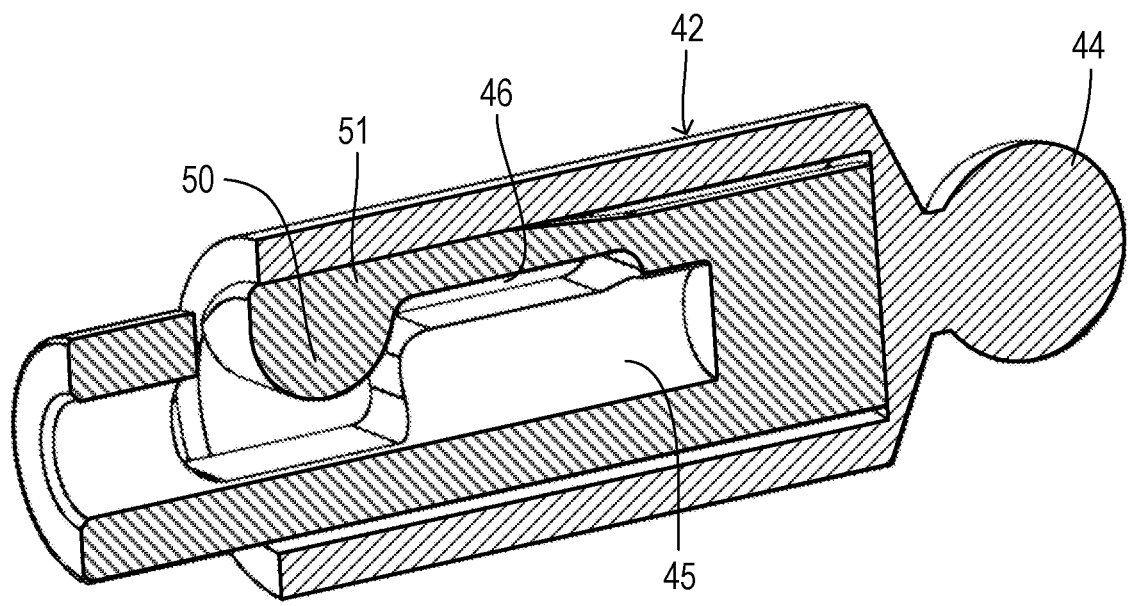
FIG. 9 is a cross-sectional, perspective view of the mounting adapter of FIG. 5.
Figure 10:
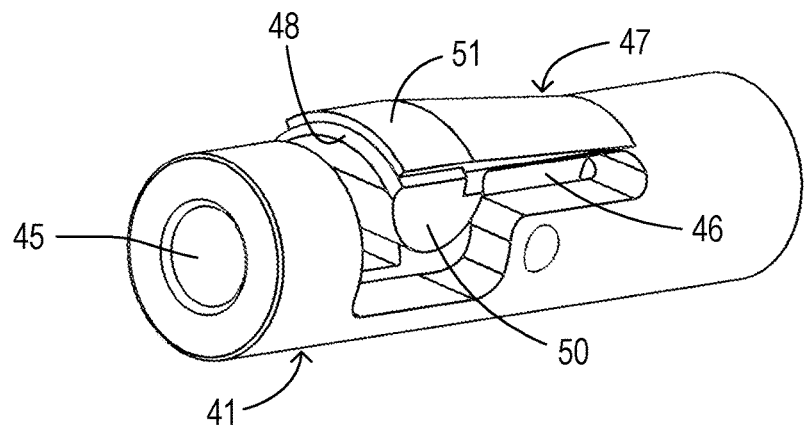
FIGS. 10 and 11 are perspective views of the receiver body of FIG. 5.
Figure 11:
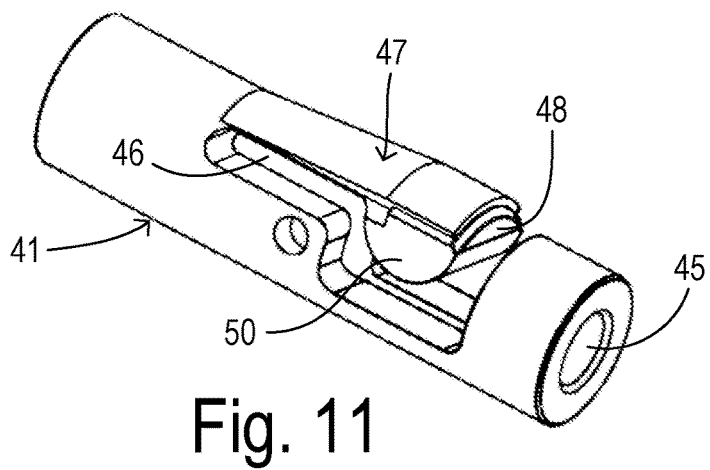
Figure 13:
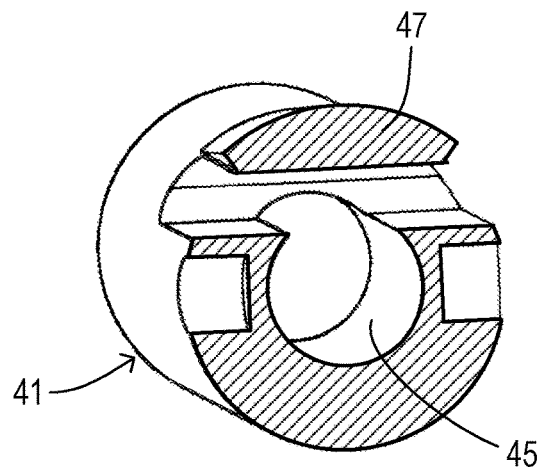
FIGS. 12 and 13 are a longitudinal cross section and a transverse cross section, respectively, of the receiver body of FIG. 5.
Figure 12:
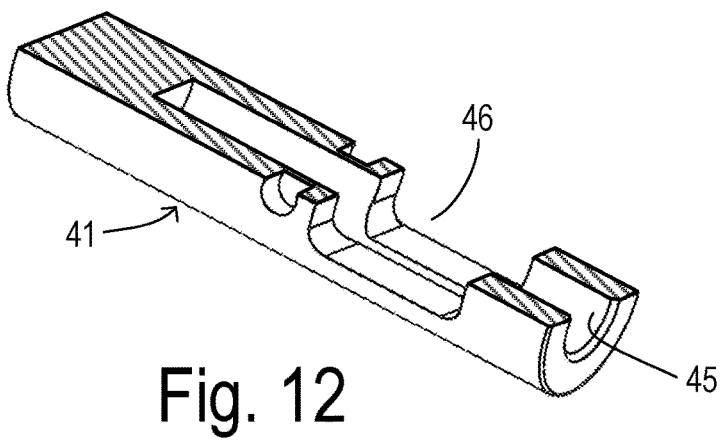
Figure 14:
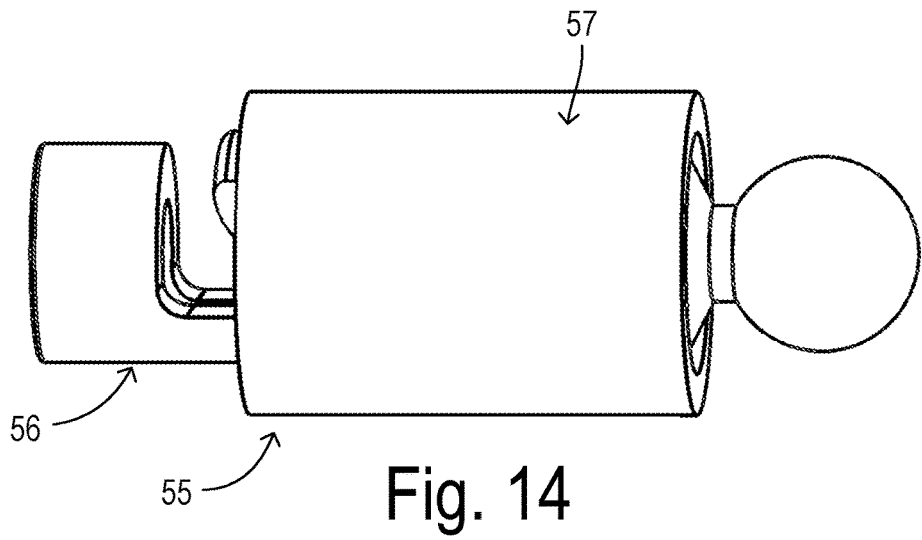
FIG. 14 is a side view of a second embodiment of a mounting adapter of the present invention.
Figure 15:
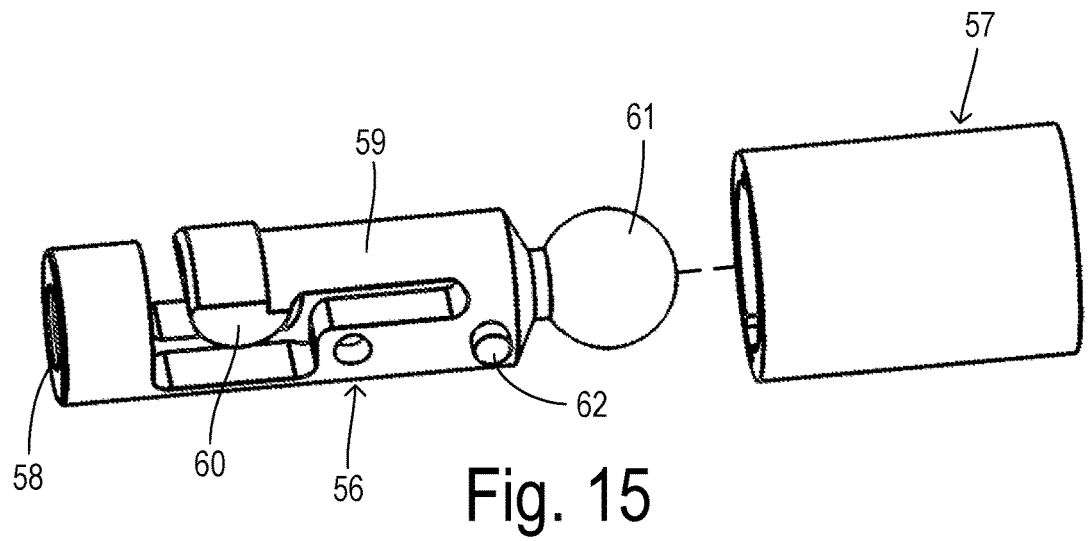
FIG. 15 is a side view of the mounting adapter of FIG. 14 with a sleeve being removed from the receiver body.
Figure 16:
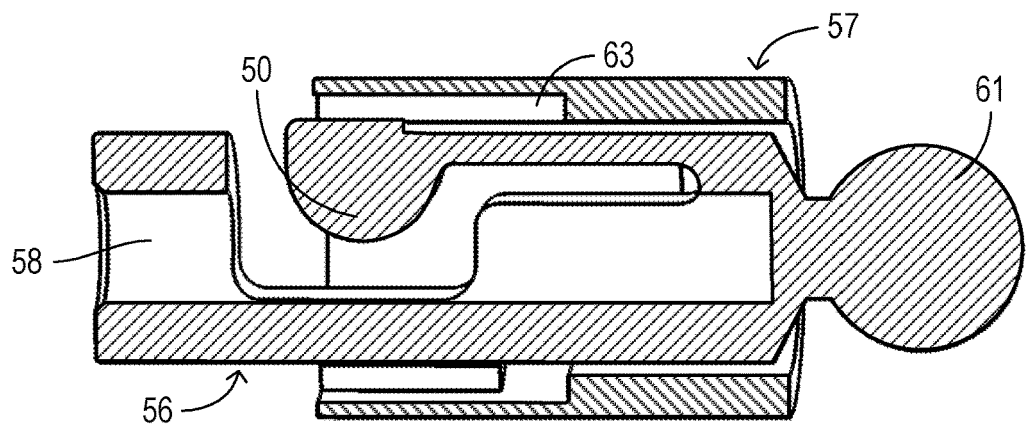
FIG. 16 is a cross-sectional view of the adapter of FIG. 14.
Figure 17:
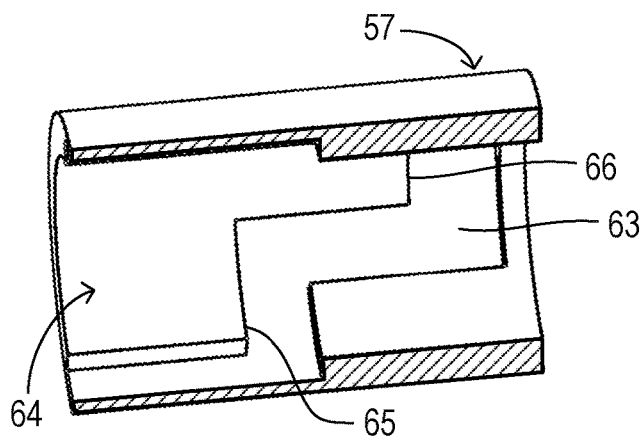
FIG. 17 is a cross-sectional view of the sleeve of FIG. 14 showing a latching groove.
Figure 18:
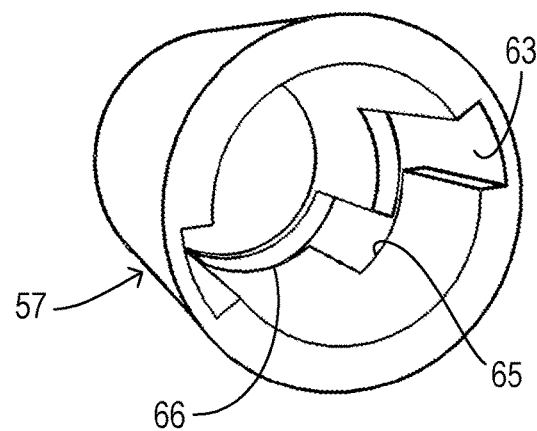
FIG. 18 is an end, perspective view of the sleeve of FIG. 14.
Figure 19:
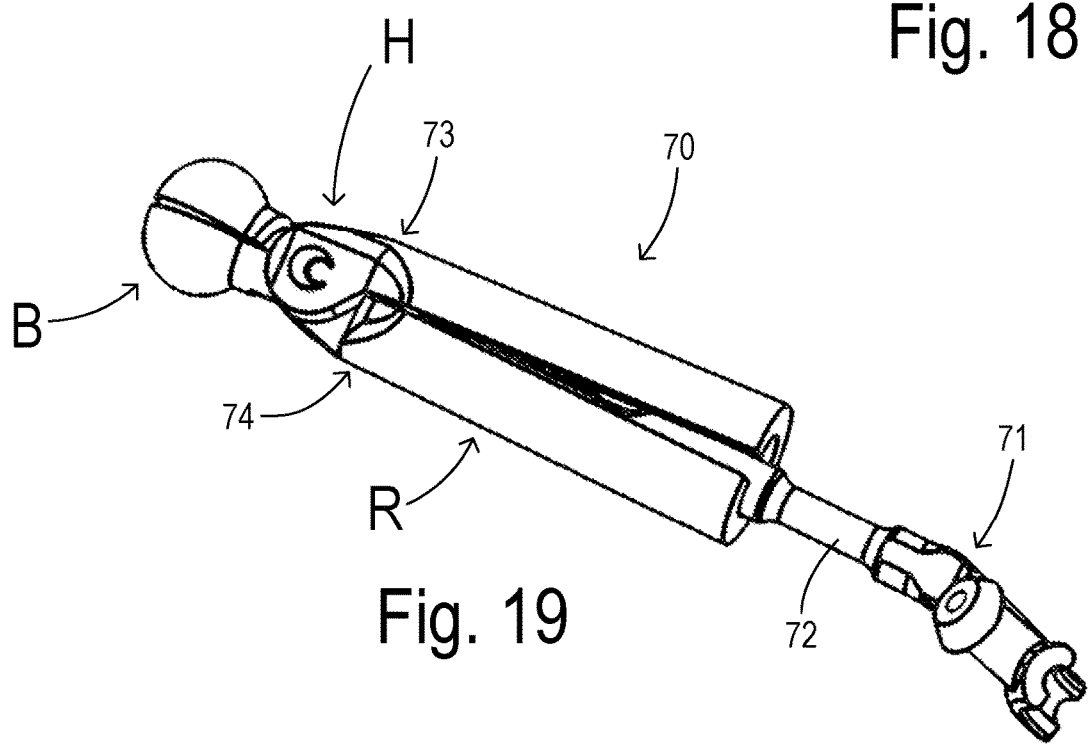
FIG. 19 is a perspective view of a third embodiment of a mounting adapter of the invention together with a shaft-type manipulator tool.

FIG. 7 shows an exploded view of an assembly including adapter 40 with manipulator tool 21 and stabilizer arm 14. Shaft 22 is inserted into bore 45 with receiver body 41 either separated from sleeve 42 (FIG. 5) or being only partially inserted into sleeve 42 so that free end 48 is free to deflect radially inward or outward. The normal rest position of detent 50 may slightly penetrate into an edge of bore 45 such that free end 48 deflects radially outward in response to insertion of the tool shaft, thereby lightly grasping the shaft. In the event that the tool shaft includes a notch, then detent 50 may snap into the notch to confirm proper placement of the tool shaft into adapter 40. Then receiver body 41 is fully slid into sleeve 42 (FIG. 6). As best shown in FIGS. 8 and 9, this embodiment uses an interference fit between sleeve 42 and lip 51. In the locked state, detent 50 is fully deflected radially into bore 45 and is in position to be compressed against the tool shaft and/or captured in a notch in the tool shaft.

Receiver body 41 and sleeve 42 may preferably be comprised of molded thermoplastic. Insertion of the parts may be a one-way interference fit that locks in place and is not easily removable. Thus, both the tool attachment and the adapter mount have a low manufacturing cost so that they can be considered disposable after a single surgical use.

FIGS. 14-18 show a second embodiment wherein an adapter mount 55 is comprised of a receiver body 56 and a hollow cylindrical sleeve 57. Receiver body 56 includes a bore 58 configured to receive the shaft of a tool attachment (not shown) and includes a cantilever spring arm 59 having a free end including a detent 60 which is configured to bear against the tool shaft to retain the tool. Receiver body 56 also includes a ball stem 61 at the end which is opposite from bore 58, wherein ball stem 61 is configured to attach with a collet of a stabilizer arm.

Cylindrical sleeve 57 is configured to interact with the free end of cantilever spring arm 59 in a way that is similar to the previous embodiment, i.e., detent 60 is compressed to a radially inward position to provide a locked state when sleeve 57 is fully installed over receiver body 60 and naturally rests at (or is free to move into) a radially outward position to provide an unlocked state when sleeve 57 is clear of the free end of spring arm 59. In order to selectably secure sleeve 57 onto receiver body 56 in the locked and unlocked states, a pair of radial pins 62 extend from diametrically opposite sides of receiver body 56 to be received in a latching groove 63 on an inner surface 64 of sleeve 57. To install sleeve 57, radial pins 62 are inserted into open ends of groove 63, and after axially advancing sleeve 57 to partially insert receiver body 56, sleeve 57 is rotated so that pins 62 are captured in a first circumferential leg 65 of groove 63. In that position, sleeve 57 is retained on receiver body 56 without radially compressing cantilever spring arm 59. After a tool attachment is inserted into bore 58, sleeve 57 is axially advanced along another axial portion of groove 63 until radial lock pins 62 can be rotated into a second circumferential leg 66 of groove 63, thereby retaining sleeve 57 in the locked state with radial compression being applied to the free end of cantilever spring arm 59.

FIGS. 19-24 show a third embodiment of a mounting adapter 70 wherein the receiver body and ball stem are mutually comprised of scissor members 73 and 74 for retaining an attachment tool attachment 71 via its mounting shaft 72. Members 73 and 74 cooperatively form a hinge joint H (FIG. 19) between a ball section B (on one longitudinal side of hinge joint H) and a receiver section R (on the other longitudinal side of hinge joint H).

Figure 20:
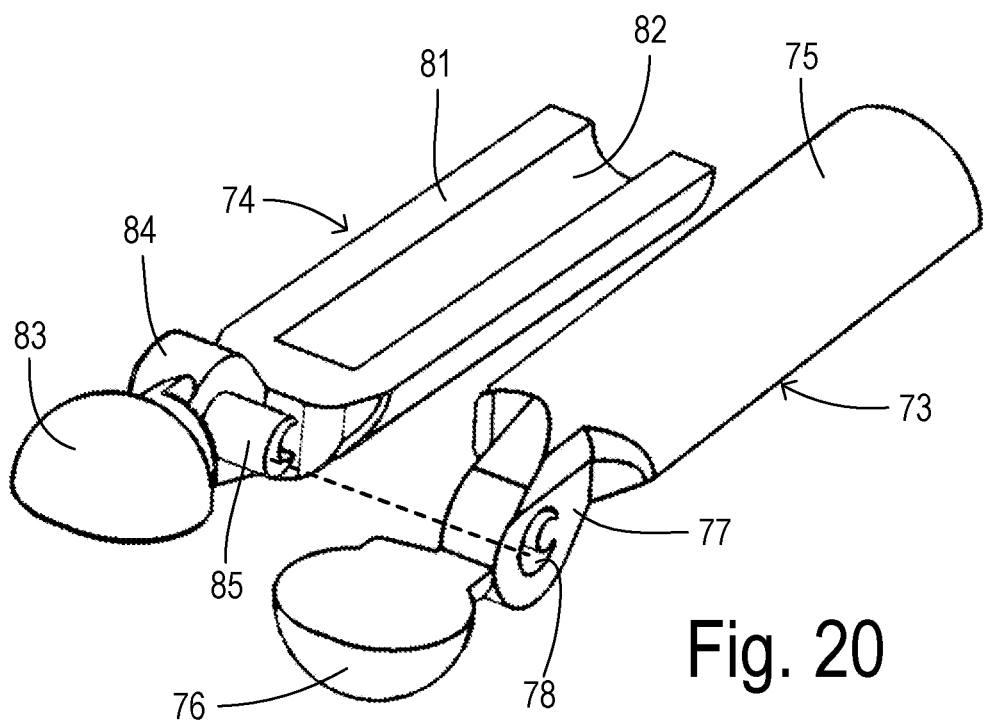
FIGS. 20 and 21 are perspective views of scissor members of the adapter of FIG. 19.
Figure 21:
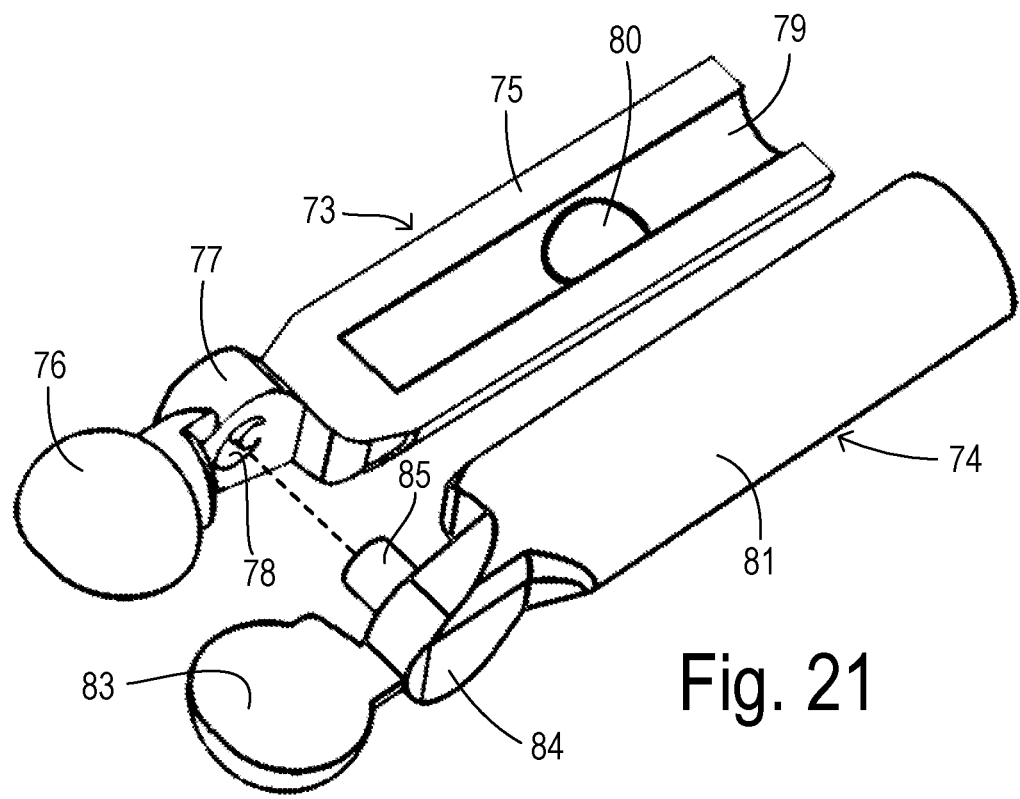
Figure 22:
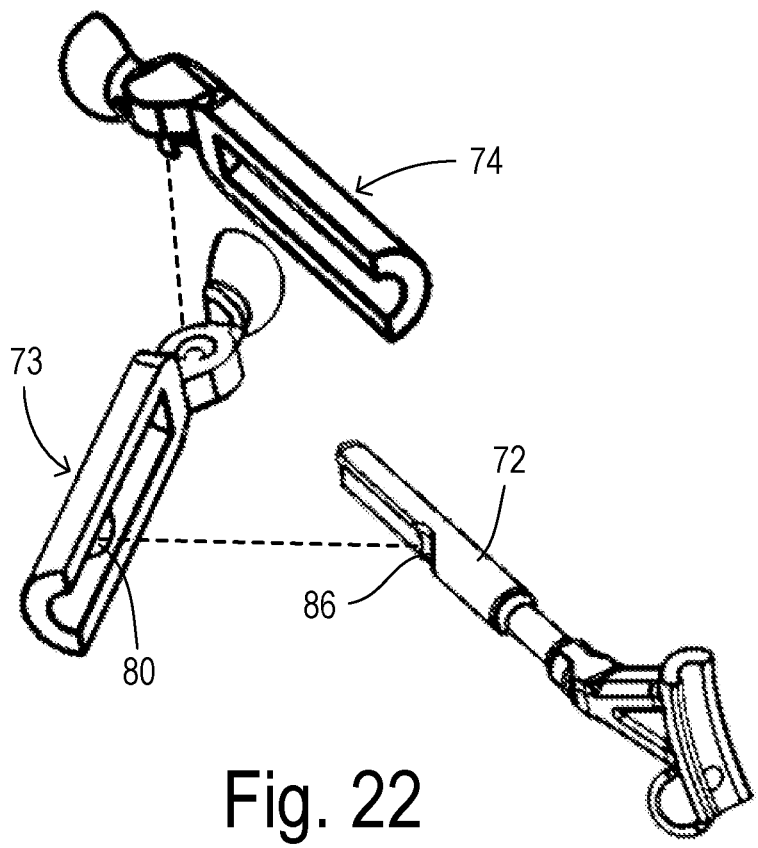
FIG. 22 is an exploded view of the adapter and tool of FIG. 19.
Figure 23:
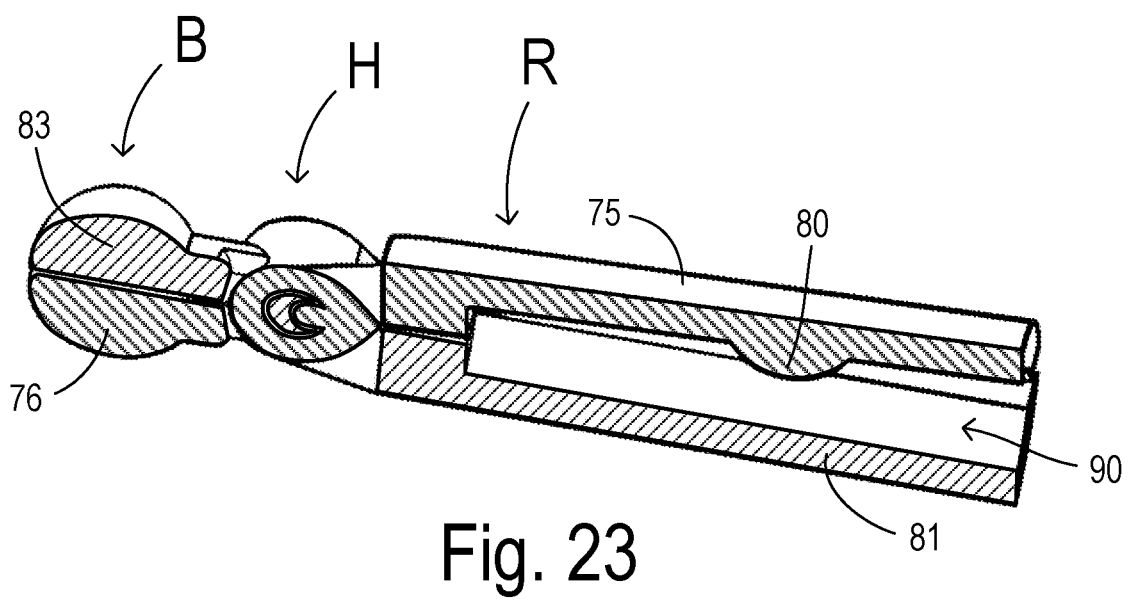
FIG. 23 is a longitudinal cross section of the adapter of FIG. 19.

As shown in greater detail in FIGS. 20 and 21, scissor member 73 includes a first hollow semicylinder section 75 extending in a first longitudinal direction from a hinge section 77 and includes a first semisphere 76 projecting in a second longitudinal direction from hinge section 77. Semicylinder section 75 has an inner wall 79. A detent 80 is formed as a bump protruding from inner wall 79. Detent 80 is configured to capture a notch 86 within tool shaft 72 (FIG. 22). Scissor member 74 includes a second hollow semicylinder section 81 with an inner wall 82 extending in the first longitudinal direction from a hinge section 84 and includes a second semisphere 83 projecting in a second longitudinal direction from hinge section 84.

Figure 24:
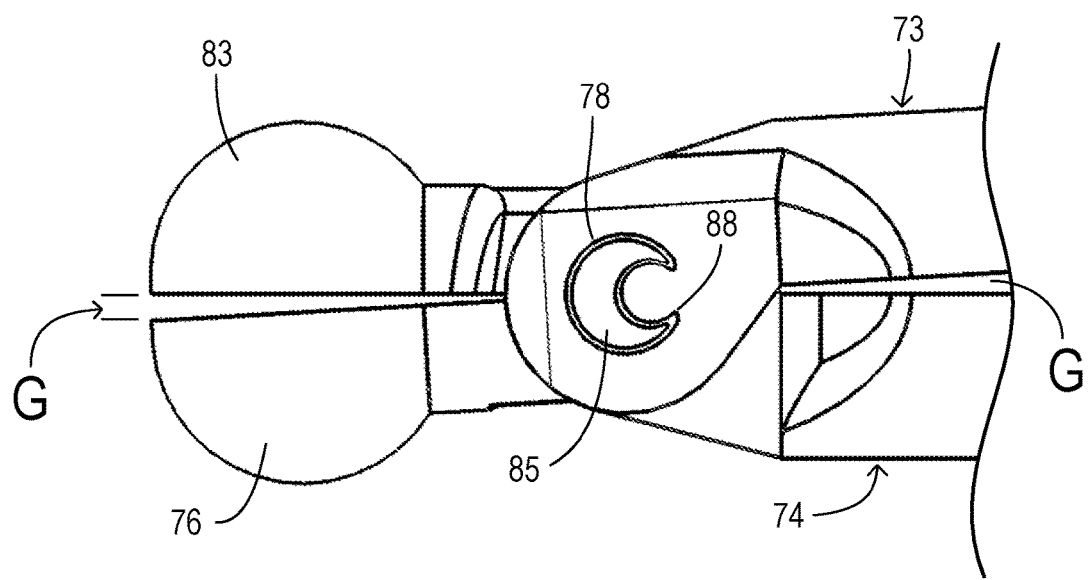
FIG. 24 is a side view showing a proximal end of the adapter of FIG. 19 in greater detail.
Figure 25:
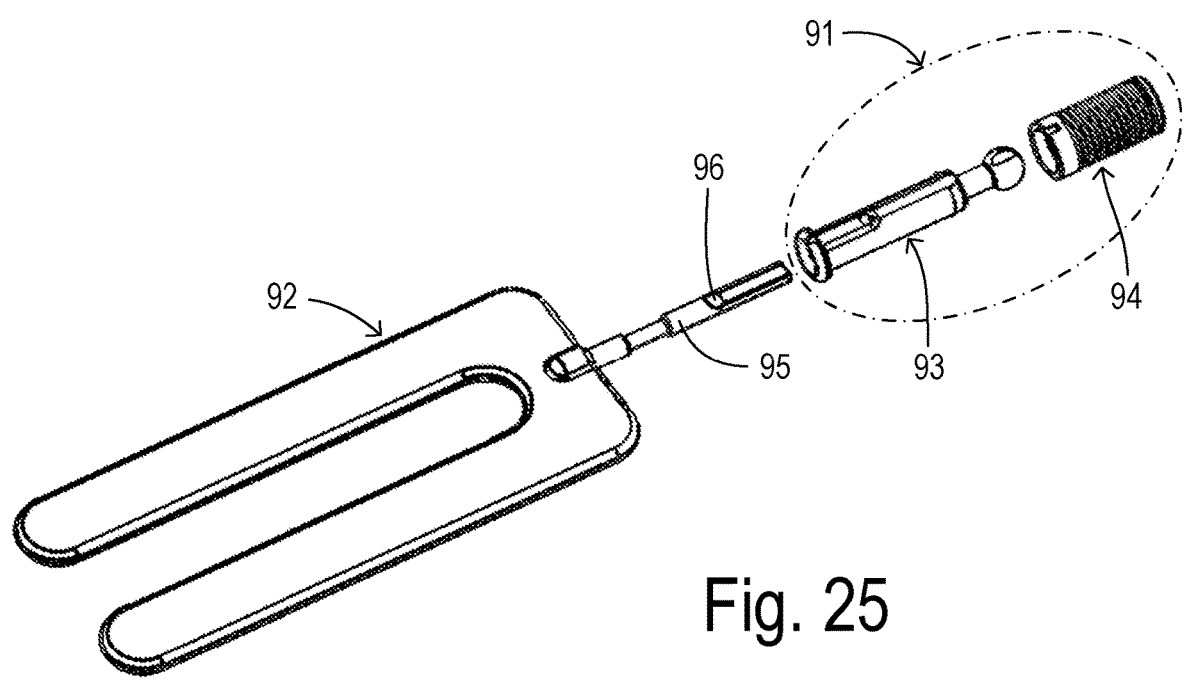
FIG. 25 is an exploded, perspective view of a fourth embodiment of a mounting adapter of the invention together with a shaft-type manipulator tool.
Figure 26:
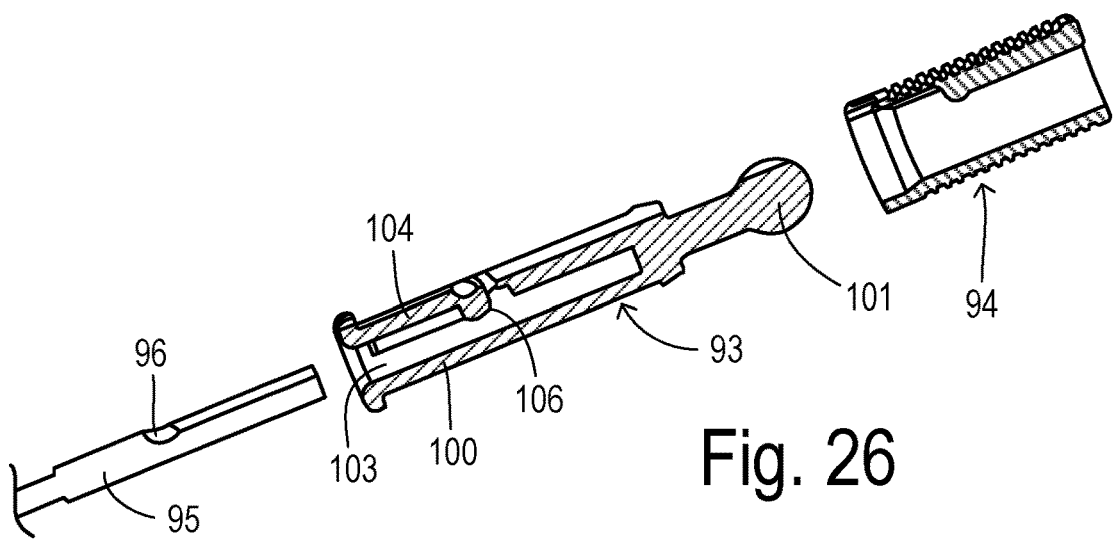
FIG. 26 is an exploded view showing the receiver body and cylindrical sleeve of FIG. 25 in cross section.
Figure 27:
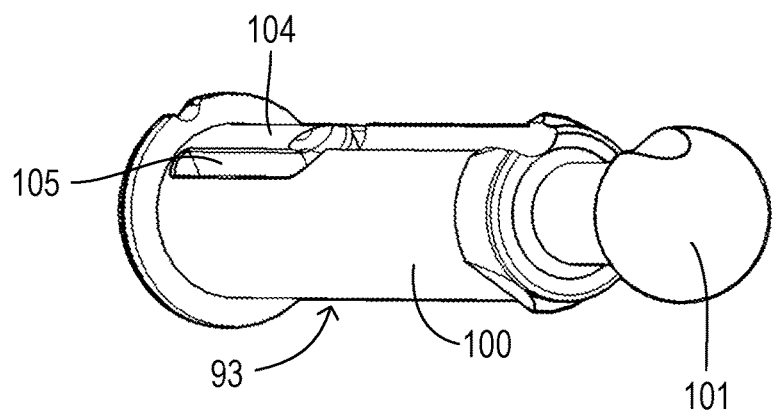
FIGS. 27 and 28 are perspective views of the receiver body of FIG. 25.
Figures 30, 31:
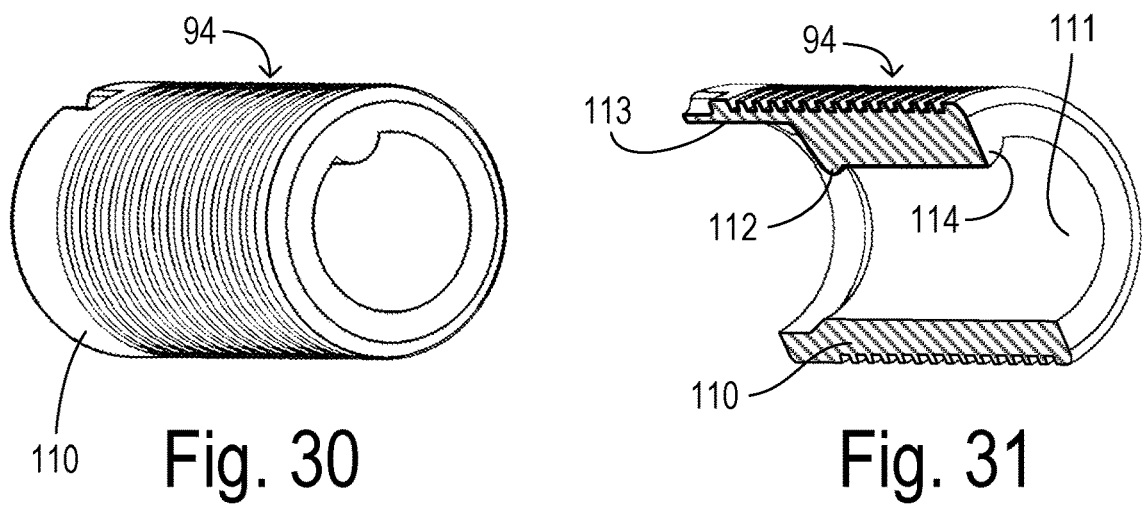
FIG. 30 is a perspective view of the sleeve of FIG. 25.
FIGS. 31 and 32 are cross-sectional, perspective views of the sleeve of FIG. 25.
Figure 28:
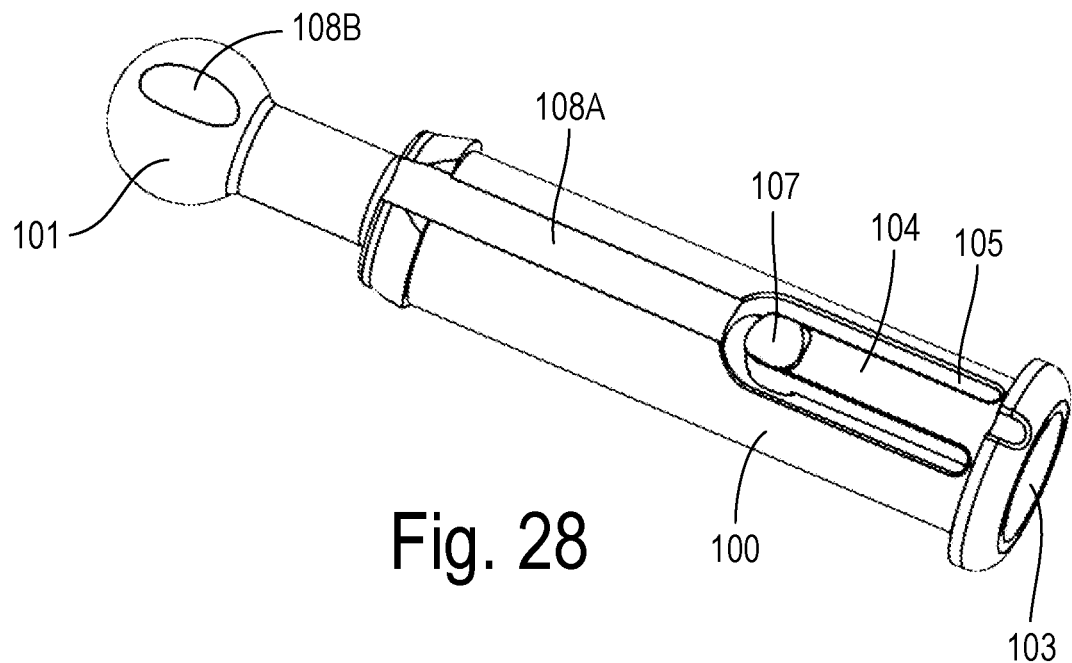
Figure 29:
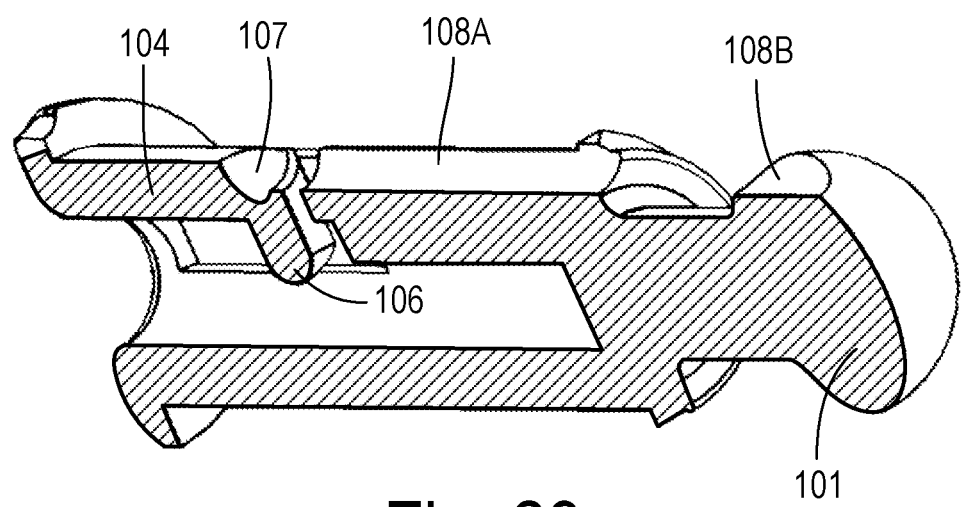
FIG. 29 is a cross-sectional view of the receiver body of FIG. 25.
Figure 32:
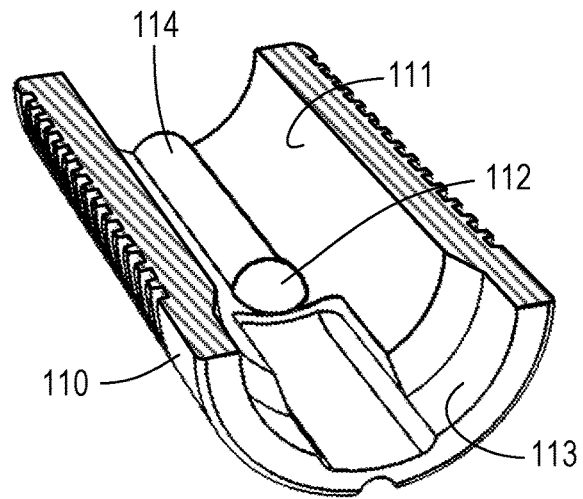
Figure 33:
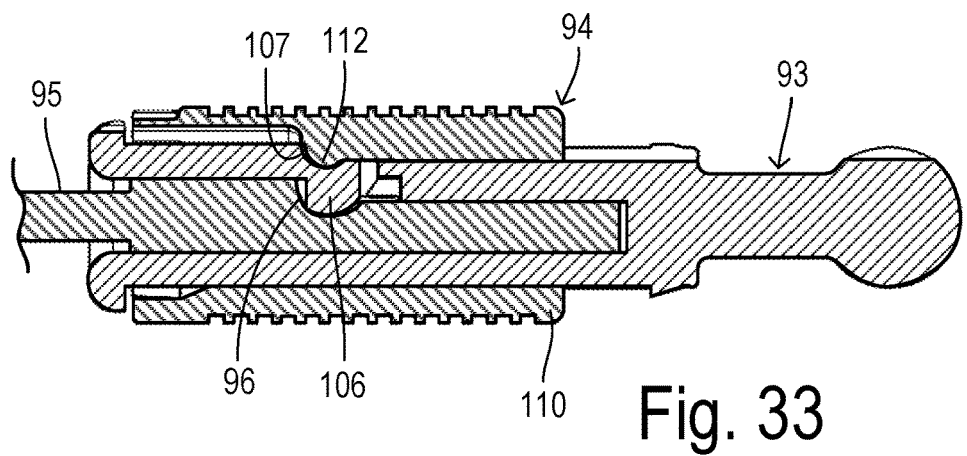
FIG. 33 is a side, cross sectional view of the adapter of FIG. 25.
Figure 34:
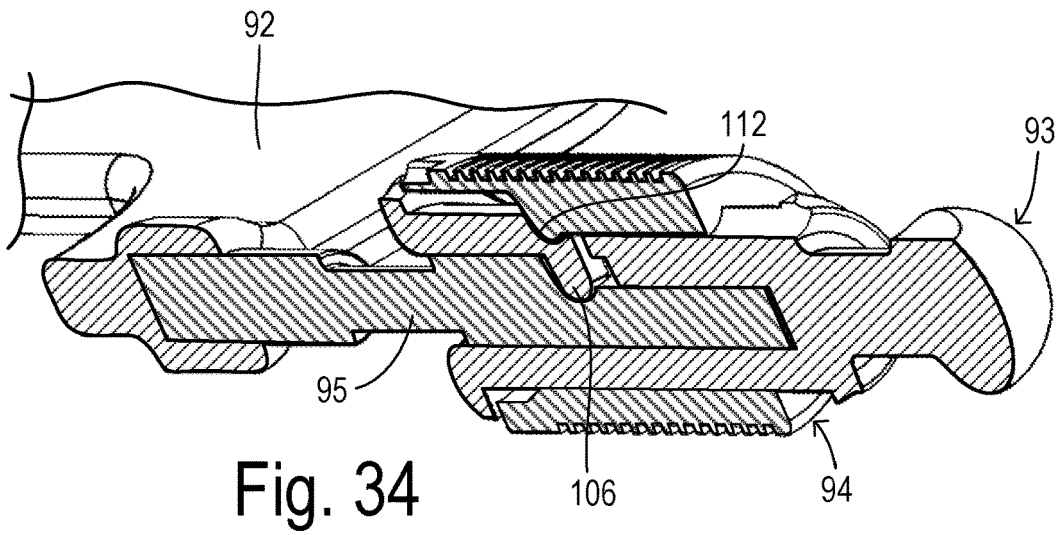
FIG. 34 is a perspective, cross-sectional view of the adapter and tool of FIG. 25.

Ball section B defines a ball stem which is comprised of first and second semispheres 76 and 83, and receiver section R defines a bore 90 which is comprised of an area within hollow semicylinder sections 75 and 81. A scissor motion at hinge joint H pivots scissor members 73 and 74 between 1) a locked state wherein semispheres 76 and 83 abut to define a spherical ball and the semicylinder sections 75 and 81 abut to define a hollow cylinder with central bore 90, and 2) a unlocked state wherein semispheres 76 and 83 and semicylinder sections 75 and 81 are respectively spaced apart by a gap G (FIG. 24). Hinge joint H includes a crescent-shaped shaft 85 extending from hinge section 84 of scissor member 74 and a crescent-shaped hole 78 within hinge section 77 of scissor member 73 which receives crescent-shaped shaft 85. Shaft 85 and hole 78 are configured to restrict a range of pivoting of hinge joint H, thereby providing a predetermined maximum size of gap G. As shown in FIG. 24, hole 78 has an inner profile that is slightly larger than an outer profile of shaft 85 to allow a controlled amount of pivot. Shapes other than a crescent shape can alternatively be used which result in a collision at an appropriate angle to control the amount of pivoting. With gap G at its maximum, shaft 72 of tool attachment 71 is easily inserted into bore 90. Then semispheres 76 and 83 can be inserted into the collet of the stabilizer arm. Tightening of the collet over semispheres 76 and 83 locks down ball section B (i.e., eliminating gap G) which also locks down semicylinders 75 and 81. Preferably, scissor members 73 and 74 are each integrally molded (e.g., of a biocompatible, sterilizable plastic) to form their respective hollow semicylinder, semisphere, and hinge section in one piece.

An outer collar (not shown) could be installed over hinge joint H after members 73 and 74 are assembled in order to keep them together during shipping and during mounting to an attachment tool and collet of a stabilizer arm. The collar could be welded to one of the scissor members at a pinch point between the two half-cylinders, for example.

FIGS. 25-34 show a fourth embodiment of a mounting adapter 91 for connecting a manipulator tool attachment 92 to a stabilizer arm. Adapter 91 includes a receiver body 93 and a sleeve 94 adapted to grasp a notch 96 in a shaft 95 extending from tool 92. Receiver body 93 has a distal socket 100 and a proximal ball stem 101. A distal flange 102 has a central opening that leads to a bore 103 which receives tool shaft 95. A cantilever spring 104 extends into a notch 105 from distal flange 102 and has a detent 106 at its proximal end extending radially inward into bore 103. On the radially outward side of the free end of cantilever spring 104, a concave dimple 107 is formed which acts as a bearing surface for compressing the free end of spring 104 radially inward. Sleeve 94 has a cylindrical body 110 with an inner surface 111. Inner surface 111 has an enlarged inner diameter 113 at a distal end for accommodating insertion of receiver body 100. Along one side of inner surface 111, a longitudinal ridge 114 and a convex bump 112 project radially inward. Convex bump 112 is configured to mate with concave dimple 107 and to compress it radially inward in order to capture notch 96. While mated, dimple 107 locks bump 112 and sleeve 94 at the distal-most position (i.e., in the locked state).

Receiver body 100 has an outer longitudinal slot 108A and 108B with a size and shape adapted to match longitudinal ridge 114 in order to guide the sliding of sleeve 94 over receiver body 100. This aligns convex bump 112 with concave dimple 107 and detent 106. Thus, by sliding ridge 114 along slot 108 in the distal direction after inserting shaft 95 such that detent 106 rests in notch 96, the sliding of sleeve 94 up to its maximum distal position locks shaft 95 in place. Thereafter, ball stem 101 can be inserted into a collet of the stabilizer arm (not shown).

What is claimed is:

1. A mounting adapter with a proximal end for interfacing with a surgical stabilizer arm and a distal end for interfacing with a tissue manipulator tool having a shaft, comprising:
   a receiver body defining a bore having an opening at the distal end for receiving the manipulator tool, wherein the receiver body includes a detent projecting radially into the bore; and
   a ball stem projecting at the proximal end and configured for insertion into a collet of the stabilizer arm;
   wherein the detent is radially displaceable between 1) a radially outward position when the adapter is in an unlocked state in which the shaft of the manipulator tool is slidable into or out of the bore and 2) a radially inward position when the adapter is in a locked state in which the detent captures the shaft of the manipulator tool;
   wherein the receiver body is comprised of first and second scissor members joined at a hinge joint, wherein the scissor members define first and second hollow semicylinder sections extending in a first longitudinal direction from the hinge joint;
   wherein the ball stem is comprised of first and second semispheres projecting from the first and second scissor members, respectively, in a second longitudinal direction from the hinge joint; and
   wherein a scissor motion at the hinge joint pivots the scissor members between 1) the locked state wherein the semispheres abut to define a sphere and the semicylinder sections abut to define a hollow cylinder and 2) the unlocked state wherein the semispheres and the semicylinder sections are respectively spaced apart by a gap.

2. The mounting adapter of claim 1 wherein the detent is comprised of a bump protruding from an inner wall of the first hollow semicylinder section.

3. The mounting adapter of claim 1 wherein the hinge joint is comprised of a crescent-shaped shaft extending from one of the first and second scissor members along a pivot axis and a crescent-shaped hole in the other one of the first and second scissor members receiving the crescent-shaped shaft, wherein the shaft and hole are configured to restrict pivoting of the hinge joint so that the semispheres separated by the gap are insertable into the collet.

4. The mounting adapter of claim 3 wherein the first scissor member is integrally molded to form the first hollow semicylinder, first semisphere, and the crescent-shaped shaft, and wherein the second scissor member is integrally molded to form the second hollow semicylinder, second semisphere, and the crescent-shaped hole.

5. A mounting adapter with a proximal end for interfacing with a surgical stabilizer arm and a distal end for interfacing with a tissue manipulator tool having a shaft, comprising:
   a receiver body defining a bore having an opening at the distal end for receiving the manipulator tool, wherein the receiver body includes a detent projecting radially into the bore, and wherein the receiver body comprises:
      a hollow cylindrical section having a notch exposing a side portion of the bore, wherein the notch is spaced away from the distal end of the receiver body; and
      a cantilever spring having a free end disposed in the notch and carrying the detent: and
   a ball stem projecting at the proximal end and configured for insertion into a collet of the stabilizer arm;
   wherein the detent is radially displaceable between 1) a radially outward position when the adapter is in an unlocked state in which the shaft of the manipulator tool is slidable into or out of the bore and 2) a radially inward position when the adapter is in a locked state in which the detent captures the shaft of the manipulator tool.

6. The mounting adapter of claim 5 wherein the free end has an unloaded position suspending the detent radially away from the bore to provide the unlocked state, and wherein the free end has a loaded position deflecting the detent into the bore to provide the locked state.

7. The mounting adapter of claim 6 further comprising a cylindrical sleeve disposed over the receiver body adapted to move longitudinally to radially compress the free end.

8. The mounting adapter of claim 7 wherein the free end of the cantilever spring extends into the notch from the distal end, and wherein the sleeve has an inner surface with a convex bump protruding radially inward that engages the free end when the sleeve is slid over the receiver body toward the distal end.

9. The mounting adapter of claim 8 wherein the free end has an outer surface forming a concave dimple configured to receive the convex bump to provide positive retention of the sleeve when the adapter is in the locked state.

10. The mounting adapter of claim 8 wherein the inner surface of the sleeve has a longitudinal ridge, wherein the receiver body has a longitudinal slot, and wherein the ridge is slidable in the slot to align the bump with the detent.

11. The mounting adapter of claim 7 wherein the sleeve has an inner surface that engages with an outer surface of the free end when the sleeve is slid over the receiver body toward the distal end, and wherein the sleeve is maintained in the locked state by an interference fit between the sleeve and the free end.

12. The mounting adapter of claim 7 wherein the sleeve has an inner surface that engages with an outer surface of the free end when the sleeve is slid over the receiver body toward the distal end, wherein the inner surface includes a latching groove, wherein the outer surface has a radial lock pin, and wherein the sleeve is maintained in the locked state by rotating the sleeve with the lock pin in the groove.

13. The mounting adapter of claim 7 wherein the ball stem is integrally formed with the receiver body.

14. The mounting adapter of claim 7 wherein the ball stem is integrally formed with the sleeve.

\* \* \* \* \*